United States Patent [19]

Borysko

[11] 4,444,927
[45] Apr. 24, 1984

[54] SUCROSE AND/OR LACTOSE NUCLEATING AGENTS FOR THE CRYSTALLIZATION OF POLYDIOXANONE

[75] Inventor: Emil Borysko, Somerville, N.J.
[73] Assignee: Ethicon, Inc., Somerville, N.J.
[21] Appl. No.: 417,780
[22] Filed: Sep. 13, 1982
[51] Int. Cl.$^3$ .......................... C08L 5/00; A61L 17/00
[52] U.S. Cl. .................................... 524/56; 128/335.5; 264/331.21; 528/354
[58] Field of Search ..................... 128/335.5; 521/908; 528/354; 524/56; 264/331.21

[56] References Cited
U.S. PATENT DOCUMENTS
4,052,988  10/1977  Doddi et al. ..................... 128/335.5

FOREIGN PATENT DOCUMENTS
2144406  3/1973  Fed. Rep. of Germany ........ 524/56

OTHER PUBLICATIONS
"Crystal Growth, Theory and Techniques"; C. H. L. Goodman, Ed.; vol. 1; Phenum Press: New York; 1974, pp. 60, 236.

Primary Examiner—George F. Lesmes
Assistant Examiner—William M. Atkinson
Attorney, Agent, or Firm—Charles J. Metz

[57] ABSTRACT

Sucrose and/or lactose is employed as a nucleating agent in polydioxanone polymer in the preparation of absorbable shaped articles made from polydioxanone.

8 Claims, 2 Drawing Figures

SUCROSE AND/OR LACTOSE NUCLEATING AGENTS FOR THE CRYSTALLIZATION OF POLYDIOXANONE

The invention relates to the use of sucrose and/or lactose nucleating agents in a process for fabricating absorbable shaped articles from polydioxanone, and to the absorbable shaped articles that can be made from said process.

BACKGROUND OF THE INVENTION

Within the last ten years or so, synthetic absorbable polymers have become widely used in surgical practice. The principal utility has been in sutures. However, shaped articles other than sutures are also beginning to become important in medical/surgical procedures. For instance, ligating clips, staples, other fastening devices, temporary support members, and the like are beginning to be fabricated from synthetic absorbable polymers so that such articles can be employed during a surgical procedure, implanted in the body to perform a function, and then will gradually be absorbed in the body after the device is no longer needed.

An important class of synthetic absorbable polymers that are starting to be employed to make absorbable shaped articles are polydioxanones. Typically, the shaped articles made from these polymers are injection molded by procedures that are analogous to well known injection molding techniques. One characteristic of polydioxanone polymers that has tended to limit production rates and has thus tended to increase the cost of shaped articles made from them, is that after the polymer has been injected into a mold, and the mold has been cooled in accordance with conventional injection molding techniques, the polymer can be very slow to crystallize. Sometimes, the polymer will tend to cool to a temperature well below its optimal crystallization temperature without solidifying. As a result, the molding cycles employed in the production of shaped articles from these polymers tend to be much slower than would be desirable.

The present invention is directed to a means for increasing the rate of solidification of polydioxanone by crystallization in a molding process utilizing said polymer.

BRIEF SUMMARY OF THE INVENTION

The invention provides a process for fabricating absorbing shaped articles of polydioxanone which comprises heating a mixture of polydioxanone plus a small amount of a finely divided sucrose and/or lactose nucleating agent, to a temperature above the crystalline melting point of the polydioxanone but below the melting point of the said nucleating agent, shaping the molten polymer containing the finely divided nucleating agent, and then cooling the mixture below the crystalline melting point of the polydioxanone, whereby an absorbable shaped article is formed containing the nucleating agent dispersed throughout the polymer.

The invention also provides an absorbable shaped article comprising polydioxanone containing a small amount of a finely divided sucrose and/or lactose nucleating agent.

DETAILED DESCRIPTION OF THE INVENTION

The synthetic absorbable polymers that are employed in this invention are polydioxanones. The polydioxanones are a known class of polymers, which are disclosed more particularly in Doddi et al., U.S. Pat. No. 4,052,988. Briefly, the polymers are produced by polymerizing either p-dioxanone or an alkyl-substituted dioxanone. Polydioxanones are comprised of recurring units of Formula I:

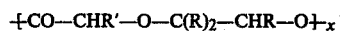

$$\{CO-CHR'-O-C(R)_2-CHR-O\}_x \qquad I$$

wherein each R' and R individually are hydrogen, methyl, or ethyl, and wherein x is a number whose average value reflects the degree of polymerization resulting in a solid polymer. The preferred polydioxanone is poly(p-dioxanone), i.e., the polymer that contains recurring units of Formula I wherein all the R' and R variables are hydrogen.

The nucleating agents that have been found to be useful in accelerating the crystallization and/or solidification rate of molten polydioxanone are sucrose and lactose. The particular value of the nucleating agents that are employed in this invention is that they have no adverse biological reaction in the body when the absorbable shaped article is absorbed since they occur naturally in tissue.

The nucleating agent is employed in a finely divided form to provide as many nucleating sites as possible. For instance, the particle size of the nucleating agents is normally within the range of from about 0.01 to about 2 microns, and preferably the maximum particle size is about 1 micron. The nucleating agents are employed in a small amount, sufficient to accelerate the crystallization rate or the solidification rate of the molten polymer as the polymer cools. The amount has not been found to be narrowly critical, but normally the proportion will be less than about one weight percent.

The nucleating agent is added to the polymer simply by mixing the two materials together. Preferably, the polymer is employed in rather finely divided form, and the nucleating agent is simply added to it with mixing. The mixture of the polymer plus nucleating agent is then employed in conventional injection molding techniques. As a result of the presence of the nucleating agent, the cycling time of injection molding of the polymers can be significantly reduced in many cases.

The examples below illustrate the practice of the invention.

EXAMPLE 1

Figure 1:
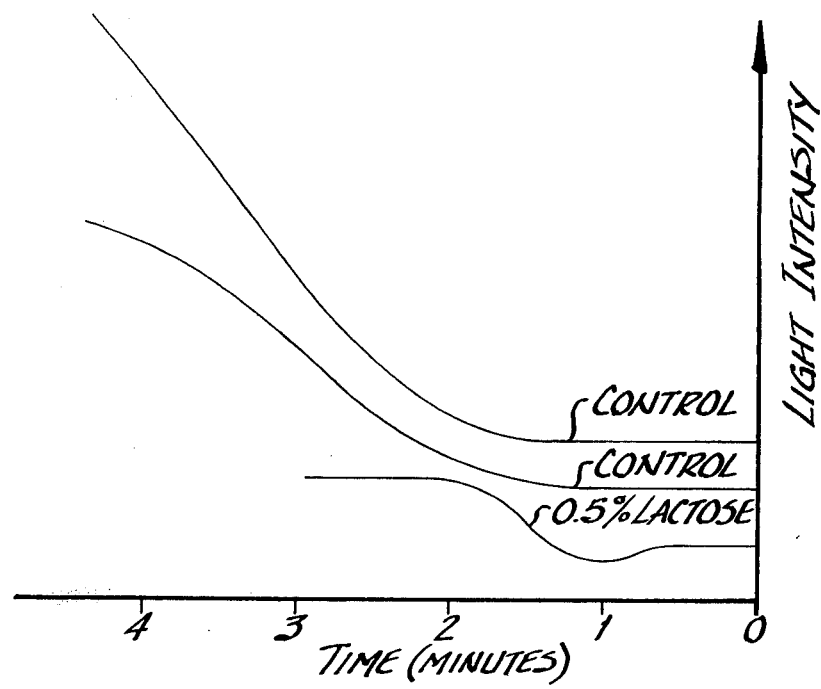
FIG. 1 is a graph of light intensity versus time for samples of the molten nucleated polymer and samples of the molten control (i.e., un-nucleated) polymer described in Example 1.

Lactose, 0.5 percent by weight, was added to four grams of poly(p-dioxanone) polymer particles, and the mixture was powdered in a Spex Freezer Mill at liquid nitrogen temperature. The mixture was then melted at 150° C. on a microscope slide, and was pressed into a thin film under a cover glass. This initial melting was done on a hot stage microscope. The sample was then transferred immediately to another hot stage microscope that was held at 55° C. While the sample was in this microscope, the rate of crystallization was observed visually and was recorded photometrically. The procedure for measuring and recording the crystallization photometrically was the following:

A light source was positioned at the bottom of the microscope. Above that, there is a polarizer. Above the polarizer there is the sample, and above the sample there is positioned an analyzer, which is another polarized filter with its plane of polarization oriented 90° to that of the bottom polarizer. Little or no light is transmitted through the analyzer until crystallization begins to occur. Light then is transmitted because the crystals are birefringent and appear very bright in the microscope field. A photocell in one of the ocular openings of the microscope senses the changes in light intensity, and a recorder is used to plot the results as shown in FIG. 1 in which light intensity is plotted versus time. The sample containing 0.5 weight percent lactose is compared with two control samples which contain no nucleating agent. In the sample containing lactose, crystallization begins at the stage where the curve dips down slightly, and is completed at the two-minute point where the curve levels out. The crystallization had not completed with either of the controls after four + minutes, since in both cases the light intensity curves were still rising. (The points on the y axis at which the curves begin were selected arbitrarily so that the several curves would not intersect each other.)

EXAMPLE 2

Figure 2:
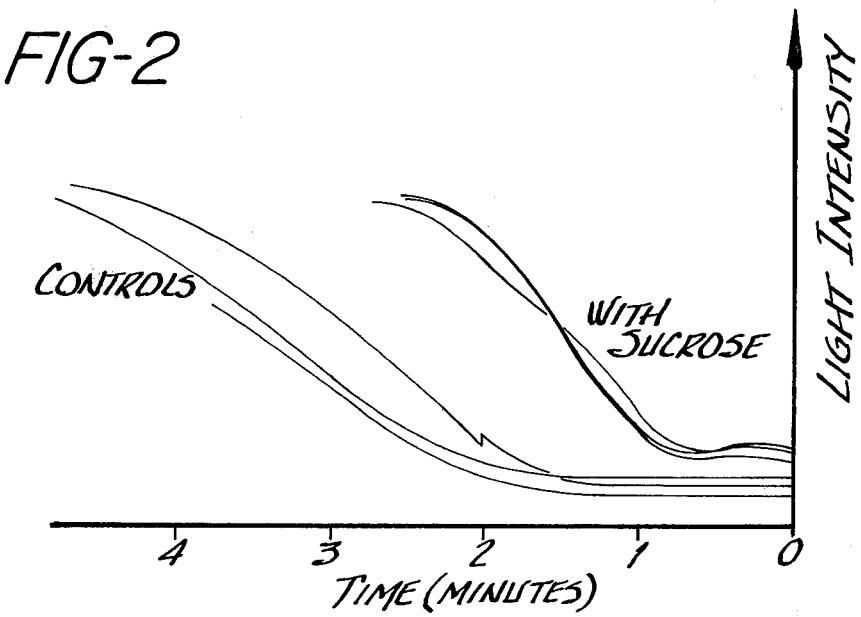
FIG. 2 is a graph of light intensity versus time for samples of the molten nucleated polymer and samples of the molten control polymers of Example 2.

By a procedure analogous to that described in Example 1, the effect of sucrose on the nucleation rate of poly(p-dioxanone) was evaluated. Three samples containing about one weight percent sucrose that had been ground in an agate mortar and pestle to an estimated particle size range of about 1–75 microns was added to molten polymer. The amount was estimated to be less than about one weight percent. The nucleated samples were melted at 150° C., flattened into thin films under a cover glass, and were quickly transferred to the second hot stage microscope that was held at 55° C. As with Example 1, the rate of nucleation was observed visually and was recorded photometrically. The results of the photometric measurement are shown in FIG. 2, which displays the results of three samples containing sucrose and three controls which contained no nucleating agent. As was the case with lactose, it is seen that sucrose accelerates the rate of crystallization quite significantly.

EXAMPLE 3

Samples of poly(p-dioxanone), both un-nucleated and containing 0.2 weight percent or 0.5 weight percent sucrose, were injection molded to try to determine whether or not the addition of the sucrose nucleating agents could reduce the cycle time. The polymer was injection molded at a barrel temperature of 120° C. into a mold maintained at 50° C. The process was used to mold ligating clips. The time from injection into the mold until the time that the mold was opened and the molded ligating clips were removed was designated as the cycle time. The lowest cycle time that was able to be used with the un-nucleated polymer was about 90 to 100 seconds. Cycle times shorter than that resulted in distortion of the parts after they were removed from the mold, because they had not sufficiently crystallized and/or solidified in the mold. However, by the addition of either 0.2 percent sucrose or 0.5 percent sucrose, the molding cycle could be reduced to as low as about 40 seconds, and still make good clips. This illustrates that the invention can be employed to reduce the molding cycle time required for producing shaped articles of polydioxanone.

What is claimed is:

1. Process for fabricating absorbable shaped articles of polydioxanone which comprises heating a mixture of polydioxanone with a small amount of a finely divided sucrose or lactose nucleating agent, to a temperature above the crystalline melting point of the polydioxanone, which temperature is below the melting temperature of the nucleating agent, shaping the molten polymer/nucleating agent mixture, and then cooling the mixture below the crystalline melting point of the polydioxanone, whereby an absorbable shaped article is formed containing the nucleating agent dispersed throughout the polymer.

2. The process of claim 1 wherein said nucleating agent is sucrose.

3. The process of claim 1 wherein the nucleating agent is lactose.

4. The process of claim 1, 2 or 3 wherein the polydioxanone is poly(p-dioxanone).

5. An absorbable shaped article comprising polydioxanone containing a small amount of a finely divided sucrose or lactose nucleating agent dispersed throughout said article.

6. The absorbable shaped article of claim 5 wherein said polydioxanone is poly(p-dioxanone).

7. The absorbable shaped article of claim 5 or 6 wherein said nucleating agent is sucrose.

8. The absorbable shaped article of claim 5 or 6 wherein said nucleating agent is lactose.

* * * * *